(12) United States Patent
Guo et al.

(10) Patent No.: US 11,419,801 B2
(45) Date of Patent: Aug. 23, 2022

(54) PERSONAL CARE COMPOSITION

(71) Applicant: Conopco, Inc., Englewood Cliffs, NJ (US)

(72) Inventors: Chenliang Guo, Shanghai (CN); Nan Huang, Shanghai (CN); Sheila Alves Rocha, Bogota, NJ (US)

(73) Assignee: CONOPCO, INC., Englewood Cliffs, NJ (US)

( * ) Notice: Subject to any disclaimer, the term of this patent is extended or adjusted under 35 U.S.C. 154(b) by 66 days.

(21) Appl. No.: 16/641,709

(22) PCT Filed: Aug. 17, 2018

(86) PCT No.: PCT/EP2018/072337
§ 371 (c)(1),
(2) Date: Feb. 25, 2020

(87) PCT Pub. No.: WO2019/042795
PCT Pub. Date: Mar. 7, 2019

(65) Prior Publication Data
US 2020/0360252 A1    Nov. 19, 2020

(30) Foreign Application Priority Data

Aug. 30, 2017 (WO) ................ PCT/CN2017/099618
Sep. 19, 2017 (EP) ..................................... 17191915

(51) Int. Cl.
| | | |
|---|---|---|
| A61K 8/36 | (2006.01) | |
| A61K 8/9778 | (2017.01) | |
| A61K 8/34 | (2006.01) | |
| A61K 8/37 | (2006.01) | |
| A61K 8/42 | (2006.01) | |
| A61K 8/67 | (2006.01) | |
| A61Q 5/00 | (2006.01) | |
| A61Q 11/00 | (2006.01) | |
| A61Q 19/08 | (2006.01) | |

(52) U.S. Cl.
CPC .............. *A61K 8/361* (2013.01); *A61K 8/347* (2013.01); *A61K 8/37* (2013.01); *A61K 8/42* (2013.01); *A61K 8/676* (2013.01); *A61K 8/9778* (2017.08); *A61Q 5/00* (2013.01); *A61Q 11/00* (2013.01); *A61Q 19/08* (2013.01); *A61K 2800/59* (2013.01); *A61K 2800/92* (2013.01)

(58) Field of Classification Search
CPC .................................................. A61Q 19/08
See application file for complete search history.

(56) References Cited

U.S. PATENT DOCUMENTS

| 8,945,636 | B2 * | 2/2015 | Sigurjonsson | ....... A61K 31/202 |
|---|---|---|---|---|
| | | | | 424/725 |
| 2008/0139649 | A1 | 6/2008 | Barrow et al. | |
| 2011/0082217 | A1 | 4/2011 | Johnson et al. | |
| 2011/0293755 | A1 | 12/2011 | Sigurjonsson et al. | |
| 2017/0087109 | A1 * | 3/2017 | Batchvarova | ........ A61K 31/201 |
| 2017/0128357 | A1 * | 5/2017 | Brilloulet | ................ A61K 8/99 |

FOREIGN PATENT DOCUMENTS

| CN | 106879718 | 6/2017 |
|---|---|---|
| DE | 102011084708 | 2/2013 |
| EP | 0139480 | 5/1985 |
| KR | 100751883 | 8/2007 |
| KR | 20170004631 | 11/2017 |
| WO | WO2011148247 | 1/2011 |
| WO | WO2011148247 | 12/2011 |
| WO | WO2015173481 | 11/2015 |

OTHER PUBLICATIONS

Search Report and Written Opinion in PCTEP2018072337; dated Nov. 6, 2018.
Yuki Yamamoto et al.; Effects of alpha-hydroxy acids on the human skin of Japanese subject: The rationale for chemical peeling; Journal of Dermatology; Jan. 1, 2006; pp. 16-22.
Kim et al.; Photoprotective and anti-skin-aging effects of eicosapentaenoic acid in human skin in vivo; Journal of Lipid Research; Feb. 7, 2006; 921-930; 47, No. 5.
Search Report and Written Opinion in EP17191915; dated Mar. 13, 2018.
IPRP2 in PCTEP2018072337; dated Nov. 13, 2019; World Intellectual Property Org. (WIPO).

\* cited by examiner

*Primary Examiner* — Mark V Stevens
*Assistant Examiner* — Alparslan Asan
(74) *Attorney, Agent, or Firm* — Stephanie Huang

(57) ABSTRACT

The invention relates to a personal care composition, more particularly to a composition for application to a topical surface that prevents or reduces inflammation. The composition could be delivered in the form of a skin, scalp, hair or oral care product, more particularly a skin care product. The benefit is delivered via a combination of a polyunsaturated fatty acid (PUFA) or ester thereof selected from docosahexaenoic acid (DHA), eicosapentaenoic acid (EPA), DHA-ethyl ester, EPA-ethyl ester, DHA-triglyceride, EPA-triglyceride, dihomogamma-Linolenic Acid (DGLA), DGLA-ethyl ester, DGLA-triglyceride or combinations thereof and a 4-substituted resorcinol compound, wherein the mole ratio of the PUFA or ester thereof to the 4-substituted resorcinol compound is 5:1 to 1:5.

9 Claims, No Drawings

PERSONAL CARE COMPOSITION

CROSS REFERENCE TO RELATED APPLICATIONS

The present application is a U.S. National Phase Application under 35 U.S.C. § 371 of International Application No. PCT/EP2018/072337, filed on Aug. 17, 2018, which claims priority to International Application No. PCT/CN2017/099618, filed on Aug. 30, 2017, and European Patent Application No. 17191915.2, filed on Sep. 19, 2017, the contents of which are incorporated herein in their entireties.

FIELD OF THE INVENTION

The invention relates to a personal care composition, more particularly to a composition for application to a topical surface of a human or animal that prevents or reduces inflammation. The composition could be delivered in the form of a skin, scalp, hair or an oral care product, more particularly a skin care product.

BACKGROUND OF THE INVENTION

Inflammation, a complicated biological host response to harmful stimuli, is a mechanism by which the host removes the stimuli and initiates the healing process for self-protection. The innate immune system for a host is the first line of defence against invading organisms in a non-specific manner. Dysregulated inflammation may cause various personal care problems including gingivitis/periodontitis (in the oral cavity), dandruff (on scalp/hair) and eczema/acnes (on skin). To assist the host organism (e.g. the human or animal) several anti-inflammatory agents either through topical application or through oral consumption have been developed and used to mitigate the above problems.

The skin experiences many conditions like aging, pigmentation, photo-damage, and skin irritation which are all accompanied by inflammation. Additionally inflammation has been implicated in many problems like skin wrinkling, acne, age spots, eczema, dandruff, and hyper-pigmentation. These problems, in addition to causing discomfort, also leave a displeasing cosmetic appearance. Many of the above problems have been treated or alleviated by use of one or more of emollients, sunscreens, anti-aging actives, or anti-microbial actives. Anti-inflammatory actives are also often included.

Thus, inflammation is a process that is manifest on the topical surface of the human or animal body in one or all of the above described conditions. The present inventors have attempted to alleviate the symptoms of the above conditions by developing combination of actives that exhibit synergistic anti-inflammatory benefits. The present invention concerns identification of actives which could be derivatized from compounds found in extracts of natural materials. Natural materials from which many actives have been extracted include several spices, ginger, turmeric, tea, grape, tomato and a host of others. The present inventors have studied combination of materials that could potentially provide synergistic anti-inflammatory activity. After extensive experimentation they found that certain specific polyunsaturated fatty acids (PUFA) in combination with 4-substituted resorcinol compounds exhibit such behaviour.

EP0138480 A1 (Efamol, 1987) discloses a product for topical application against inflammatory and pruritic conditions of the skin which comprises 0.01 to 30% by weight of a dermatological tar or tar-based preparation and 0.01 to 30% by weight of γ-linolenic acid (GLA) or dihomo-γ-linolenic acid (DGLA) as such or in the form of an active derivative thereof. The product in addition may comprise zinc compounds, salicylates, sulphur, hydrocortisone or other steroids, iodohydroxyquinoline, lauryl sulphate, resorcinol, or benzoyl peroxide.

KR20170004631 (Kim H) discloses a cosmetic composition comprises *Rhodiola* extract, pine bark extract and marinolanic acid-4-butylresorcinol emulsion in a weight ratio of 1-2:1-2:1-2.

WO2011148247 A1 (Kresis EHF) discloses a stabilized formulation for skin care, wound care and/or other tissue healing applications. The formulation stabilizes omega-3 PUFA and is constituted of the omega-3 PUFA in combination with tocopherol (Vitamin E), ascorbic acid (Vitamin C), herb extract, and a fat-soluble antioxidant.

US2017128357 A1 (J&J) discloses topical gel cream composition comprising: (a) an oil soluble UV filter; (b) an emulsifier selected from the group consisting of glyceryl stearate, steareth-21, and polyacrylate-13/polyisobutene/polysorbate 20; (c) an emollient selected from the group consisting of pentylene glycol, caprylyl methicone, dicaprylyl carbonate, and octyldodecyl neopentanoate; and (d) a thickener selected from the group consisting of ammonium acrylolydimethyltaurate/vinylpyrrolidone copolymer, sodium acrylolydimethyltaurate/vinylpyrrolidone copolymer, and sodium polyacrylate; wherein the composition comprises greater than 20 weight % of oils.

The present inventors have found that a specific combination of PUFAs along with 4 substituted resorcinol delivers the anti-inflammatory benefits while the other additional compounds disclosed in the above publication do not.

It is thus an object of the present invention to provide for a personal care composition where the actives exhibit synergistic anti-inflammatory behavior.

It is another object of the present invention where at least one of the actives can be derived from a compound extractable from a natural source.

SUMMARY OF THE INVENTION

According to the first aspect of the present invention there is provided a personal care composition comprising:
 (i) a polyunsaturated fatty acid (PUFA) or ester thereof selected from docosahexaenoic acid (DHA), eicosapentaenoic acid (EPA), DHA-ethyl ester, EPA-ethyl ester, DHA-triglyceride, EPA-triglyceride, dihomogamma-Linolenic Acid (DGLA), DGLA-ethyl ester, DGLA-triglyceride or combinations thereof;
 (ii) a 4-substituted resorcinol compound; and
 (iii) a cosmetically acceptable base, wherein the mole ratio of the PUFA or ester thereof to the 4-substituted resorcinol compound is 5:1 to 1:5.

According to another aspect of the present invention there is provide a non-therapeutic method of reducing or preventing inflammation on a topical surface of a human or animal body comprising the step of applying the composition of the invention on to the desired surface.

According to another aspect of the invention is disclosed non-therapeutic use of a composition of the first aspect for reducing or preventing inflammation on a topical surface of a human or animal body.

According to yet another aspect of the present invention is disclosed non-therapeutic use of a composition of the first aspect of the invention for improving a skin condition including skin aging, pigmentation, photo-damage and skin irritation and inflammation.

According to yet another aspect of the invention is disclosed a non-therapeutic method of improving a skin condition including skin aging, pigmentation, photo-damage and skin irritation and inflammation comprising the step of applying a composition of the first aspect of the invention on to the desired surface.

In accordance with yet further aspect of the invention is disclosed a personal care composition comprising:
(i) a polyunsaturated fatty acid (PUFA) or ester thereof selected from docosahexaenoic acid (DHA), eicosapentaenoic acid (EPA), DHA-ethyl ester, EPA-ethyl ester, DHA-triglyceride, EPA-triglyceride, dihomogamma-Linolenic Acid (DGLA), DGLA-ethyl ester, DGLA-triglyceride or combinations thereof;
(ii) a 4-substituted resorcinol compound; and,
(iii) a cosmetically acceptable base, wherein the mole ratio of the PUFA or ester thereof to the 4-substituted resorcinol compound is 5:1 to 1:5, for use to reduce or prevent inflammation on a topical surface of a human or animal body.

In accordance with yet further aspect of the invention is disclosed a personal care composition comprising:
(i) a polyunsaturated fatty acid (PUFA) or ester thereof selected from docosahexaenoic acid (DHA), eicosapentaenoic acid (EPA), DHA-ethyl ester, EPA-ethyl ester, DHA-triglyceride, EPA-triglyceride, dihomogamma-Linolenic Acid (DGLA), DGLA-ethyl ester, DGLA-triglyceride or combinations thereof;
(ii) a 4-substituted resorcinol compound; and,
(iii) a cosmetically acceptable base, wherein the mole ratio of the PUFA or ester thereof to the 4-substituted resorcinol compound is 5:1 to 1:5, for use to improve a skin condition including skin aging, pigmentation, photo-damage and skin irritation and inflammation.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the final composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By 'A topical composition' or a 'skin care composition' as used herein, is meant to include a composition for topical application to the skin of mammals, especially humans. Such a composition could be of the leave-on or of the wash-off/rinse-off type. By a leave-on composition is meant a composition that is applied to the desired skin surface and left on for a period of time (say from one minute to 24 hours) after which it may be wiped or rinsed off with water, usually during the regular course of personal washing. By a wash-off/rinse off composition is meant a composition that is applied to the desired skin surface for a shorter period of time say of the order of seconds or minutes and usually contains sufficient surfactants that aids in cleaning the surface which may be rinsed off with copious amounts of water. The composition may also be formulated into a product which is applied to a human body for improving the appearance, cleansing, odor control or general aesthetics. The composition of the present invention can be in the form of a liquid, lotion, cream, foam, scrub, gel or stick form and may be delivered through a roll-on device or using a propellant containing aerosol can. "Skin" as used herein is meant to include skin on any part of the body e.g., neck, chest, back, arms, underarms, hands, legs, buttocks and scalp. When the product is used for the underarms it is usually called a deodorant product or a deo product. A class of deodorant product is the so called anti-perspirant (AP) product which contains an AP active which when applied to the axilla of an individual delivers anti-perspirancy and deodorancy benefits.

By a 'Hair Care Composition" as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and wash-off shampoos, conditioners, shower gels or toilet bar. The composition of the present invention is preferably a wash-off composition, especially preferred being a shampoo or a conditioner and most preferably a shampoo.

"Water-insoluble", as used herein, refers to the solubility of a material in water at 25° C. and atmospheric pressure being 0.1% by weight or less.

The personal care composition of the invention comprises a polyunsaturated fatty acid (PUFA) or ester thereof selected from docosahexaenoic acid (DHA), eicosapentaenoic acid (EPA), DHA-ethyl ester, EPA-ethyl ester, DHA-triglyceride, EPA-triglyceride, dihomogamma-Linolenic Acid (DGLA), DGLA-ethyl ester, DGLA-triglyceride or combinations thereof; and a 4-substituted resorcinol compound; and a cosmetically acceptable base.

DHA and EPA are naturally enriched in fish oil, especially in marine fish, where their presence can make up over 60% of the fatty acids. A process called rendering, which is comprised of heating in solvent and separation steps, is the common traditional way of extracting fish oil. More recently, supercritical extraction is introduced to reduce the damaging effect of solvent/heating (Sathivel, S. (2010) *Fish Oil Extraction, Purification, and its Properties, in Handbook of Seafood Quality, Safety and Health Applications*). Triglyceride is the natural form in which DHA and EPA exist in fish oil. They are often hydrolyzed into free fatty acids, and subsequently made into products in such form, or further derivatised into ethyl esters and even phospholipids.

Other sources of DHA and EPA, such as n–3 PUFA, include eggs, meat, and microalgae designed to produce such PUFA through biological fermentation. Also, flaxseed (linseed) is enriched with alpha-linolenic-acid (ALA), which can potentially be a precursor of DHA and EPA.

DGLA is rarely found in dietary sources, only in trace level in certain animal products. Evening primrose (*Oenothera*) oil is the most commonly known natural source of DGLA. The majority of DGLA supply comes from industrial production, through biological approaches using yeast, fungus, or algae. Similar to DHA and EPA, free fatty acid form of DGLA can be derivatized into triglycerides or ethyl esters for application. DHA, EPA, and DGLA are all long chain PUFAs, exist in liquid form under room temperature conditions and are susceptible to oxidation and hydrogenation. When being oxidized, there can be odor generated as volatile products.

DHA, EPA, and DGLA have important biological functions, as they are all considered essential fatty acids. They mainly participate in the lipid regulatory system for immunity, by acting as substrates for the synthesis of lipid mediators of inflammation or wound healing. They are also important for the maintenance of neural network, especially during the developmental phase of the brain. Deficiency in these PUFAs has been associated with risk for cardiovascular disease, mental health issue, as well as immune dysregulation.

Preferably the compositions of the invention include PUFA or the ester thereof 0.01 to 10 wt %, more preferably from 0.1 to 5 wt % PUFA or the ester thereof. The preferred polyunsaturated fatty acids or the ester thereof are DHA, EPA, DGLA or DGLA ethyl ester.

The 4-substituted resorcinol compound is preferably a 4-linear alkyl resorcinol, 4-branched alkyl resorcinol, 4-cycloalkyl resorcinol, mixtures thereof and acylated forms thereof. Preferred 4-substituted resorcinols suitable for use in the compositions of the present invention are 4-methyl resorcinol, 4-ethyl resorcinol, 4-propyl resorcinol, 4-isopropyl resorcinol, 4-butyl resorcinol, 4-pentyl resorcinol, 4-hexyl resorcinol, 4-heptyl resorcinol, 4-octyl resorcinol, 4-nonyl resorcinol, 4-decyl resorcinol, 4-undecyl resorcinol, 4-dodecyl resorcinol, 4-cyclopentyl resorcinol, 4-cyclohexyl resorcinol, 4-cycloheptyl resorcinol, 4-cycloactyl resorcinol and mixtures thereof.

The most preferred 4-substituted resorcinols are 4-ethyl resorcinol, 4-propyl resorcinol, 4-isopropyl resorcinol, 4-butyl resorcinol, 4-pentyl resorcinol and 4-hexyl resorcinol.

Resorcinol is the 1,3-isomer (or meta-isomer) of benzenediol.

Resorcinol is a phenolic compound having two hydroxyl groups in the benzene structure. The reactivity, coupled with three reactive positions for the electrophilic substitution reactions and two hydroxyl groups for etherification and esterification reactions, offers enormous possibilities for resorcinol to develop various derivatives for numerous applications. Chemical compounds derived from resorcinolic derivatives are potent and effective medicines. Resorcinol compounds were developed and employed in the treatment of various skin conditions including those associated with tyrosinase enzymes. 4-substituted resorcinols such as hexyl and butyl groups have very good tyrosinase activity-inhibiting effect. (J Eur Accd Dermatol Venereol. 2013 January; 27 Suppl 1:19-23. doi: 10.1111/jdv.12051; J Eur Acad Dermatol Venereol. 2013 January; 27 Suppl 1:19-23. doi: 10.1111/jdv.12051.)

The composition of the invention preferably comprises 0.001 to 10 wt %, more preferably 0.001 to 3 wt %, further more preferably 0.01 to 2 wt %, even further more preferably 0.05 to 1.5 wt % and optimally from 0.05 to 1.2 wt % of 4-substituted resorcinol compound.

The mole ratio of the PUFA or an ester thereof to the 4-substituted resorcinol compound is from 5:1 to 1:5 preferably from 1:1 to 1:5.

The composition of the invention is preferably in the form of a skin, scalp or hair care product. The cosmetically acceptable base preferably comprises water, oil, surfactant, emulsion, gel or combinations thereof. The cosmetically acceptable base in such products generally comprises one or more of water, oil, and surfactant and is generally in the form of an emulsion, gel or combinations thereof.

The composition of the invention is used for skin care. The cosmetically acceptable base in such cases may be a liquid or solid material. Typically, base is present in an amount ranging from 10 to 99.9%, more preferably from 20 to 95%, most preferably from 40 to 85% by total weight of the composition including all ranges subsumed therein. It is particularly preferred that the cosmetically acceptable carrier includes water. Water is preferably included in an amount from 30 to 90%, more preferably from 30 to 85%, most preferably from 30 to 80% by total weight of the composition. Besides water, suitable carrier classes include silicones, polyhydric alcohols, hydrocarbons, triglycerides and thickening powders.

The skin care composition could be in any form including toners, lotions, creams, mousses, scrub, serum or gel that is suitable for topical application to the skin. The composition could be either a leave-on product such as skin lotions, creams, antiperspirants, deodorants, lipsticks, foundations, mascara, sunless tanners and sunscreen lotions or a rinse-off product such as shower gels and toilet bars. It is preferred that the composition is a skin lotion or a cream.

The composition of the invention preferably also comprises an emollient oil that act as a co-solvent. Suitable emollient oils include, for example, ester of alkoxylated aromatic alcohol with fatty carboxylic acid, esters of polyglycols or diols with fatty carboxylic acid such as caprylic/capric triglyceride, ester of fatty alcohol and fatty acid, alkoxylated derivative of benzyl alcohol and mixtures thereof. Preferably the emollient oil is caprylic/capric triglyceride.

Typically, such compositions comprise co-solvent in an amount from 0.01 to 10 wt %, more preferably from 0.1 to 8 wt %, most preferably from 1 to 6 wt %, based on the total weight of the composition and including all ranges subsumed therein.

The composition of the invention may additionally comprise sunscreen agents such as inorganic sunscreens. For example, zinc oxide, titanium dioxide, iron oxide, silica such as fumed silica. The amount of such sunscreen agents is preferably from 0.1 to 5 wt % by weight of the composition.

The composition of the invention may comprise a UV-A sunscreen agent selected from the group consisting of a dibenzoylmethane derivative, a triazine derivative, a benzophenone derivative and mixtures thereof. In a preferred embodiment, the UV-A sunscreen agent comprises or is a dibenzoylmethane derivative, for example, butyl methoxydibenzoylmethane (sold under the trade name Parsol 1789).

Typically, the composition of the present invention comprises from 0.1 to 15% by weight of the UV-A sunscreen agent, more preferably from 0.1 to 10%, most preferably from 1 to 5%, based on the total weight of the composition.

The composition of the invention may also comprise a UV-B sunscreen agent. Suitable UV-B sunscreen agent of the invention is selected from the group consisting of a benzophenone, an anthranilate, a salicylate, a cinnamate, a camphor, benzylidene malonate, a triazone, and derivatives thereof. In a preferred embodiment, the UV-B sunscreen agent comprises or is a cinnamate derivative, for example, ethylhexyl methoxycinnamate (sold under the trade name Parsol MCX).

Typically, the composition of the invention preferably comprises from 0.1 to 20% by weight of the UV-B sunscreen agent, more preferably from 0.5 to 18%, most preferably from 1 to 15%, based on the total weight of the composition.

A skin lightening agent may also be incorporated into the composition of the invention. Suitable skin lightening agents other than Vitamin B3 and its derivatives (e.g. niacin, nicotinic acid, niacinamide) are kojic acid, arbutin, tranexamic acid, placental extract, ascorbic acid and its derivatives (e.g. magnesium ascorbyl phosphate, sodium ascorbyl phosphate, ascorbyl glucoside, and ascorbyl tetraisopalmitates), aloe extract, ammonium lactate, azelaic acid, citrate esters, ellagic acid, glycolic acid, green tea extract, hydroquinone, lemon extract, linoleic acid, vitamins like vitamin B6, vitamin B12, vitamin C, vitamin A, a dicarboxylic acid, hydroxycarboxylic acid like lactic acid and their salts (e.g. sodium lactate) or a mixture thereof. Typically, the skin lightening agent is present in an amount from 0.1 to 10%, more preferably from 0.2 to 5%, most preferably from 0.3 to 3% by weight of the composition.

The composition of the invention may also comprise other ingredients which are common in the art to enhance physical properties and performance. Suitable ingredients include but are not limited to humectants, thickeners, opacifiers, binders, colorants and pigments, pH adjusting agents, preservatives, optics, perfumes, viscosity modifiers, biological additives, buffering agents, conditioners, natural extracts, essential oils and skin benefit agents including other anti-inflammatory agents, cooling agents, antiperspirant agents, anti-aging agents, anti-acne agents, anti-microbial agents and antioxidants.

When the personal care composition is delivered for oral care, it includes a cosmetically acceptable base which comprises an abrasive, a thickener, a humectant and an orally acceptable surfactant.

Preferably, the composition of the invention is a composition for hair care. It is especially useful for preventing or alleviating the symptoms of dandruff. One medium through which this may be delivered is that of a shampoo. The composition of the invention especially shampoos are formulated with an anionic surfactant e.g. an alkyl sulphate and/or ethoxylated alkyl sulfate surfactant. These anionic surfactants are preferably present at a level of from 1 to 20%, preferably 2 to 16%, further more preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium.

Shampoo compositions preferably comprise one or more further anionic cleansing surfactants which are cosmetically acceptable and suitable for topical application to the hair.

The compositions of the invention preferably additionally comprise an amphoteric surfactant preferably a betaine surfactant, more preferably an alkyl amidopropyl betaine surfactant for example cocamidopropyl betaine. In a preferred embodiment, the composition comprises from 0.1 to 10 wt. %, preferably from 0.5 to 8 wt. %, more preferably from 1 to 5 wt. % of a betaine surfactant To enhance deposition of actives from compositions of the invention especially shampoos, cationic polymers are generally included therein. In accordance with the present invention too, it is preferred that the composition of the invention additionally includes 0.01 to 2.0% of a cationic polymer. The cationic polymer is preferably guar hydroxypropyl trimonium chloride. Guar polymer predominantly contains galactomannan polymer chains. This polymer is available at various molecular weights and degree of cationic substitutions depending on how much guar is hydrolysed and cationised. Preferably the compositions of the invention comprise 0.04 to 0.5 wt %, more preferably 0.08 to 0.25 wt % by weight of the composition cationic polymer.

When conditioning benefits are to be delivered through the composition of the invention the composition is called a hair conditioner. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Amount of the silicone in the compositions of the invention, where present, may range from 0.1 to 10 wt. %, preferably from 0.1 to 8 wt. %, more preferably from 0.3 to 5 wt. % by weight of the hair care compositions.

The pH of the compositions of the invention is preferably equal to or higher than 4.0, more preferably in the range of 5.0 to 7.0.

The hair conditioning composition usually comprises conditioning surfactants selected from cationic surfactants, used singly or in admixture. Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1% to 5%, preferably 0.5 to 2.5% by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

The level of fatty alcohol in conditioners of the invention will generally range from 0.5 to 10%, preferably from 0.1% to 8%, more preferably from 0.2% to 7%, most preferably from 0.3% to 6% by weight of the composition Hair care compositions whether delivered as shampoos or conditioners usually comprise an anti-dandruff agent. The most preferred anti-dandruff agent for use in the composition of the invention is a zinc based anti-dandruff agent preferably zinc pyrithione.

Shampoo composition as per the invention preferably additionally comprises a conazole fungicide. Preferably the conazole fungicide is selected form ketoconazole, climbazole or mixtures thereof. The azole fungicide is preferably included in 0.01 to 2%, more preferably 0.025 to 0.75% by weight of the composition. The presence of a conazole fungicide is believed to improve the deposition of zinc pyrithione.

The invention will now be illustrated with the help of the following non-limiting examples.

EXAMPLES

Examples 1 to 13: Anti-Inflammation Efficacy of DHA and 4-Hexyl Resorcinol (HR) in THP-1 Invitro Assay The following procedure was used to test the anti-inflammation efficacy of the various actives alone as well as in combination.

In the examples, HR means hexyl resorcinol, DHA means docosahexaenoic acid.
(i) $5 \times 10^5$ THP-1 monocytes were placed into 24-well plates, with 100 nM 12-myristate 13-acetate (PMA) in the culture media to differentiate the cells.
(ii) After 72 hours differentiation, treatments as follows were applied to the cells. All the treatments from (3) to (11) were together with LPS-1 µg/ml:
(1) control; (2) LPS-1 µg/ml; (3) Dex-50 nM; (4) DHA-200 µM; (5) DHA-100 µM; (6) DHA-20 µM; (7) HR-50 µM; (8) HR-25 µM; (9) HR-100 µM; (10) HR-10 µM; (11) DHA-100 µM+HR-50 µM; (12) DHA-100 µM+HR-25 µM; (13) DHA-20 µM+HR-100 µM (14) DHA-20 µM+HR-10 µM.
(iii) After 24 hours incubation the supernatants were collected.
(iv) Then IL-6 concentration was tested in the supernatant by BD Elisa kit.

The results, in terms of concentration of IL-6 as a % of that obtained for LPS, is given in Table-1 below. The lower the percentage, the higher the anti-inflammatory potential. The CI value (combination index) of the various combinations is also less than 1 indicating synergism.

TABLE 1

| Example No. | Details of the Composition | Mole ratio of DHA to HR | % of LPS | Std. dev | CI value |
|---|---|---|---|---|---|
| 1 | LPS | — | 100 | | |
| 2 | 100 µM of DHA | — | 14.7 | 3.7 | |
| 3 | 20 µM of DHA | — | 58.5 | 3.2 | |
| 4 | 50 µM of HR | — | 41.1 | 9.3 | |
| 5 | 25 µM of HR | — | 54.5 | 6.4 | |
| 6 | 100 µM of HR | — | 41.1 | 9.3 | |
| 7 | 10 µM of HR | — | 63.1 | 0.8 | |
| 8 | 100 µM of DHA + 50 µM of HR | 2:1 | 5.3 | 2.1 | <1 |
| 9 | 100 µM of DHA + 25 µM of HR | 4:1 | 6.4 | 2.2 | <1 |
| 10 | 20 µM of DHA + 100 µM of HR | 1:5 | 13.7 | 2.2 | <1 |
| 11 | 20 µM of DHA + 10 µM of HR | 2:1 | 45.0 | 0.9 | <1 |

The data in Table above indicates that a combination of DHA with 4-hexyl resorcinol at various concentrations (and various mole ratios) exhibits synergistic anti-inflammatory behaviour with the CI value (combination index) of the various combinations was less than 1, which indicated synergy between the polyunsaturated fatty acid and the 4-substituted resorcinol.

Examples 12 to 24: Anti-Inflammation Efficacy of Combination of DHA with 4-HR and in Combination with Zinc Chloride at Various Other Concentrations Zinc chloride is included as a comparative example as this active is disclosed as an additional ingredient in EP0138480 A1.

The data below is expressed in % IL-6 inhibition rate in Table-2 below.

Further information about the experiment nos 12 to 24 is as follows:
Example 12: Vehicle control with LPS (1 µg/mL) stimulation
Example 13, 14, 15, 16: DHA at 100, 50, 25 or 12.5 µM alone with LPS (1 µg/mL) stimulation.
Example 17, 18, 19, 20: HR at 25, 12.5, 6.25 or 3.125 µM alone with LPS (1 µg/mL) stimulation.
Example 21: Combination of 100 µM DHA and 25 µM of HR.
Example 22: Combination of 50 µM DHA and 12.5 µM of HR.
Example 23: Combination of 25 µM DHA and 6.25 µM of HR.
Example 24: Combination of 12.5 µM DHA and 3.125 µM of HR.
Example 25, 26, 27, 28: $ZnCl_2$ at 25, 12.5, 6.25 or 3.125 µM alone with LPS (1 µg/mL) stimulation.
Example 29: Combination of 100 µM DHA and 25 µM of $ZnCl_2$.
Example 30: Combination of 50 µM DHA and 12.5 µM of $ZnCl_2$.
Example 31: Combination of 25 µM DHA and 6.25 µM of $ZnCl_2$.
Example 32: Combination of 12.5 µM DHA and 3.125 µM of $ZnCl_2$.

TABLE 2

| Example no. | Details of the Composition | Mole ratio of DHA to the active | % of LPS | Std. dev | CI value |
|---|---|---|---|---|---|
| 12 | LPS | — | 100 | | |
| 13 | 100 μM of DHA | — | 9.9 | 0.9 | |
| 14 | 50 μM of DHA | — | 29.0 | 2.1 | |
| 15 | 25 μM of DHA | — | 48.8 | 0.9 | |
| 16 | 12.5 μM of DHA | — | 63.1 | 1.2 | |
| 17 | 25 μM of HR | — | 43.0 | 4.6 | |
| 18 | 12.5 μM of HR | — | 55.4 | 5.7 | |
| 19 | 6.25 μM of HR | — | 60.3 | 4.1 | |
| 20 | 3.125 μM of HR | — | 66.4 | 4.9 | |
| 21 | 100 μM of DHA + 25 μM of HR | 4:1 | 4.2 | 0.2 | <1 |
| 22 | 50 μM of DHA + 12.5 μM of HR | 4:1 | 14.5 | 1.5 | <1 |
| 23 | 25 μM of DHA + 6.25 μM of HR | 4:1 | 31.5 | 2.6 | <1 |
| 24 | 12.5 μM of DHA + 3.125 μM of HR | 4:1 | 46.7 | 3.0 | <1 |
| 25 | 25 μM of $ZnCl_2$ | — | 93.4 | 8.9 | — |
| 26 | 12.5 μM of $ZnCl_2$ | — | 96.3 | 7.8 | — |
| 27 | 6.25 μM of $ZnCl_2$ | — | 97.7 | 4.8 | — |
| 28 | 3.125 μM of $ZnCl_2$ | — | 91.6 | 5.9 | — |
| 29 | 100 μM of DHA + 25 μM of $ZnCl_2$ | 4:1 | 5.8 | 0.4 | >1 |
| 30 | 50 μM of DHA + 12.5 μM of $ZnCl_2$ | 4:1 | 31.3 | 1.9 | >1 |
| 31 | 25 μM of DHA + 6.25 μM of $ZnCl_2$ | 4:1 | 53.2 | 2.8 | >1 |
| 32 | 12.5 μM of DHA + 3.125 μM of $ZnCl_2$ | 4:1 | 63.9 | 5.5 | >1 |

The data in the table above indicates that at a mole ratio of 4:1 at various concentrations of the actives, the combination as per the invention i.e. DHA and 4-HR shows synergy while a combination of DHA with Zinc chloride does not appear to be synergistic as is evident from the CI value.

Examples 33 to 52: Anti-Inflammation Efficacy of Combination of DHA with Certain Other Actives Outside the Invention Experiments were carried out, according to the procedure described earlier, at various concentrations of DHA along with certain other actives outside the invention viz. BOP (benzoyl peroxide) and SDS (sodium dodecyl sulphate). These actives have been disclosed as additional ingredients in EP0138480 A1. The data below is expressed in % IL-6 inhibition rate in Table-3 below.

Example 33, 34, 35, 36: DHA at 100, 50, 25 or 12.5 μM alone with LPS (1 μg/mL) stimulation.

Example 37, 38, 39, 40: BPO at 25, 12.5, 6.25 or 3.125 μM alone with LPS (1 μg/mL) stimulation.

Example 41: Combinations of 100 μM DHA and 25 μM of BPO.

Example 42: Combination of 50 μM DHA and 12.5 μM of BPO.

Example 43: Combination of 25 μM DHA and 6.25 μM of BPO.

Example 44: Combination of 12.5 μM DHA and 3.125 μM of BPO.

Example 45, 46, 47, 48: SDS at 25, 12.5, 6.25 or 3.125 μM alone with LPS (1 μg/mL) stimulation.

Example 49: Combinations of 100 μM DHA and 25 μM of SDS.

Example 50: Combination of 50 μM DHA and 12.5 μM of SDS.

Example 51: Combination of 25 μM DHA and 6.25 μM of SDS.

Example 52: Combination of 12.5 μM DHA and 3.125 μM of SDS.

TABLE 3

| Example no. | Details of the Composition | Mole ratio of DHA to the active | % of LPS | Std. dev | CI value |
|---|---|---|---|---|---|
| 33 | 100 μM of DHA | — | 10.7 | 1.3 | |
| 34 | 50 μM of DHA | — | 36.0 | 4.9 | |
| 35 | 25 μM of DHA | — | 56.8 | 9.0 | |
| 36 | 12.5 μM of DHA | — | 72.0 | 7.7 | |
| 37 | 25 μM of BPO | — | 103.4 | 11.4 | |
| 38 | 12.5 μM of BPO | — | 100.6 | 8.6 | |
| 39 | 6.25 μM of BPO | — | 102.7 | 9.4 | |
| 40 | 3.125 μM of BPO | — | 95.1 | 6.7 | |
| 41 | 100 μM of DHA + 25 μM of BPO | 4:1 | 7.4 | 0.5 | >1 |
| 42 | 50 μM of DHA + 12.5 μM of BPO | 4:1 | 27.5 | 1.7 | >1 |
| 43 | 25 μM of DHA + 6.25 μM of BPO | 4:1 | 48.5 | 5.4 | >1 |
| 44 | 12.5 μM of DHA + 3.125 μM of BPO | 4:1 | 69.4 | 4.1 | >1 |
| 45 | 25 μM of SDS | — | 84.6 | 2.9 | — |
| 46 | 12.5 μM of SDS | — | 86.1 | 5.5 | — |
| 47 | 6.25 μM of SDS | — | 81.3 | 6.4 | — |
| 48 | 3.125 μM of SDS | — | 80.5 | 4.8 | — |
| 49 | 100 μM of DHA + 25 μM of SDS | 4:1 | 6.8 | 0.3 | >1 |
| 50 | 50 μM of DHA + 12.5 μM of SDS | 4:1 | 25.0 | 2.1 | >1 |
| 51 | 25 μM of DHA + 6.25 μM of SDS | 4:1 | 45.0 | 2.8 | >1 |
| 52 | 12.5 μM of DHA + 3.125 μM of SDS | 4:1 | 60.4 | 6.8 | >1 |

The data in the Table 3 above indicates that the combination of DHA with actives outside the invention like benzoyl peroxide and sodium dodecyl sulphate (also known as sodium lauryl sulphate) do not exhibit synergy.

The invention claimed is:

1. A personal care composition comprising:
   (i) 0.01 to 10% of docosahexaenoic acid (DHA) by weight of the personal care composition;
   (ii) 4-hexyl resorcinol and,
   (iii) a cosmetically acceptable base,
   wherein the mole ratio of the docosahexaenoic acid (DHA) to the 4-hexyl resorcinol compound is 5:1 to 1:5.

2. The composition as claimed in claim 1, comprising 0.01 to 5% docosahexaenoic acid (DHA) thereof by weight of the composition.

3. The composition as claimed in claim 1, comprising 0.01 to 10% 4-hexyl resorcinol compound by weight of the composition.

4. The composition as claimed in claim 1, wherein the cosmetically acceptable base comprises water, oil, surfactant, an emulsifying agent, a gelling agent or combinations thereof.

5. The composition as claimed in claim 1, wherein said composition is in the form of an oral care, or a skin, scalp or hair care product.

6. A non-therapeutic method of reducing or preventing inflammation on a topical surface of a human or animal body comprising the step of applying the composition as claimed in claim 1 on to the surface.

7. The non-therapeutic method as claimed in claim 6 wherein the composition further comprises niacinamide.

8. The non-therapeutic method as claimed in claim 6 wherein the composition further comprises sunscreen.

9. The non-therapeutic method, as claimed in claim 6 wherein the composition further comprises green tea extract, ascorbic acid or both.

\* \* \* \* \*